(12) United States Patent
Chen

(10) Patent No.: US 8,899,980 B2
(45) Date of Patent: Dec. 2, 2014

(54) BONE POWDER FILLING TOOL FOR DENTAL IMPLANT

(71) Applicant: Star Generation Limited, Apia (WS)

(72) Inventor: Roger Chen, New Taipei (TW)

(73) Assignee: Star Generation Limited, Apia (WS)

( * ) Notice: Subject to any disclaimer, the term of this patent is extended or adjusted under 35 U.S.C. 154(b) by 20 days.

(21) Appl. No.: 13/845,731

(22) Filed: Mar. 18, 2013

(65) Prior Publication Data

US 2014/0045141 A1    Feb. 13, 2014

Related U.S. Application Data

(63) Continuation-in-part of application No. 13/487,374, filed on Jun. 4, 2012, now abandoned.

(51) Int. Cl.
| | | |
|---|---|---|
| *A61C 3/02* | (2006.01) | |
| *A61C 1/08* | (2006.01) | |
| *A61C 8/00* | (2006.01) | |

(52) U.S. Cl.
CPC . *A61C 1/087* (2013.01); *A61C 3/02* (2013.01); *A61C 8/0089* (2013.01)
USPC .......................................................... 433/165

(58) Field of Classification Search
CPC ............ A61C 3/02; A61C 3/025; A61C 3/03; A61C 3/04; A61C 1/082; A61C 1/085; A61C 8/0092; A61C 8/0089; A61B 17/1615; A61B 17/1617; A61B 17/1635; B23B 51/06; B23B 2260/072; B23B 2251/408
USPC ........................... 408/229, 59, 56; 606/77–80
See application file for complete search history.

(56) References Cited

U.S. PATENT DOCUMENTS

| | | | | |
|---|---|---|---|---|
| 5,816,807 A | * | 10/1998 | Matsutani et al. | 433/165 |
| 6,863,529 B2 | * | 3/2005 | Strong et al. | 433/165 |
| 7,704,075 B2 | * | 4/2010 | Breguet | 433/102 |

* cited by examiner

*Primary Examiner* — Yogesh Patel
(74) *Attorney, Agent, or Firm* — Guice Patents PLLC

(57) ABSTRACT

A bone powder filling tool includes a handle connectable to a rotary dental instrument, and a bone powder propelling bit located one end of the handle. The bone powder propelling bit has opposing top end portion and bottom end portion, bone powder transferring grooves spirally extending around the periphery thereof from the top end portion to the bottom end portion, and bone powder propelling threads extending around the periphery thereof at different elevations for rapidly and uniformly propelling bone powder into the space between the sinus floor and the cortical bone to increase the thickness of the cortical bone in favor of the process of the subsequent tooth implanting, helping the doctor in charge of the operation save operating time and physical strength.

7 Claims, 9 Drawing Sheets

A - A

BONE POWDER FILLING TOOL FOR DENTAL IMPLANT

CROSS REFERENCE TO RELATED APPLICATIONS

The present invention is a continuation-in-part of U.S. patent application Ser. No. 13/487,374.

BACKGROUND OF THE INVENTION

1. Field of the Invention

The present invention relates to dental implant technology and more particularly, to a bone powder filling tool for dental implant, which facilitates filling bone powder in the designated cortical bone area rapidly and uniformly.

2. Description of the Related Art

When an implant receives a lateral torque generated by a non-axial force after a dental implant surgery, a high stress will be produced. Therefore, the angular direction of implant displacement is quite important in a dental implant surgery. However, cortical bone thickness is another factor must be taken into account. Increasing the cortical bone thickness can significantly reduce stress around the implant. Because of this reason, a gum condition check is necessary before implant displacement. If the thickness of the cortical bone is found insufficient, filling of bone powder to lift the cortical bone thickness will be necessary.

For the purpose of increase the thickness of the cortical bone 11 at the area to be implanted with the tooth in a sinus floor 10, the sinus floor shall be performed with a surgical operation of osteotomy, such as shown in FIG. 1, an upper opening 11 shall be formed by drilling on a cortical bone 11. Then, as shown in FIG. 2, the sinus floor 10 is separated and lifted from the opening 12, and then, bone powder 13 is filled in a space between the sinus floor 10 and the cortical bone 11 to increase the thickness of the cortical bone 11 in favor of the process of the subsequent tooth implanting.

A conventional bone powder filling tool 14, as shown in FIG. 3, comprises a handle 15 having on its one end a pushing needle 16 for filling bone powder below the sinus floor 10. However, this tool renders the action of filling bone powder hard and slow, hence time of operation is increased, not only a patient feels more uncomfortable, but also a doctor in charge of the operation feels the operation is a time and physical strength extremely consumptive work.

SUMMARY OF THE INVENTION

The present invention has been accomplished under the circumstances in view. It is main object of the present invention to provide a bone powder filling tool for dental implant, which facilitates rapid tooth implanting, helping a doctor in charge of the operation save operating time and physical strength.

It is another object of the present invention to provide a bone powder filling tool for dental implant, which effectively shortens the time the patient suffers from pain.

It is still another object of the present invention to provide a bone powder filling tool for dental implant, which enables bone powder to be filled in a space between the sinus floor and the cortical bone rapidly and uniformly to increase the thickness of the cortical bone in favor of the process of the subsequent tooth implanting.

To achieve these and other objects of the present invention, a bone powder filling tool comprises a handle connectable to a rotary dental instrument, and a bone powder propelling bit located one end of the handle. The bone powder propelling bit comprises opposing top end portion and bottom end portion, bone powder transferring grooves spirally extending around the periphery thereof from the top end portion to the bottom end portion, and bone powder propelling threads extending around the periphery thereof at different elevations for rapidly and uniformly propelling bone powder into the space between the sinus floor and the cortical bone to increase the thickness of the cortical bone in favor of the process of the subsequent tooth implanting, helping the doctor in charge of the operation save operating time and physical strength.

Preferably, each bone powder transferring groove extends spirally around the periphery of the bone powder propelling bit from the top end portion to the bottom end portion.

Preferably, the bone powder propelling bit comprises a plurality of bone powder transferring grooves spirally extending around the periphery thereof and kept apart from one another.

Further, the bone powder propelling bit has a transverse (radial) width gradually reducing from the top end portion toward the bottom end portion. Further, the bone powder propelling threads extend around the periphery of the bone powder propelling bit at different elevations and configured for propelling an applied bone powder in a direction from the top end portion toward the bottom end portion.

Further, the bottom end portion of the bone powder propelling bit is preferably sleek, blunt-nosed.

Other advantages and features of the present invention will be fully understood by reference to the following specification in conjunction with the accompanying drawings, in which like reference signs denote like components of structure.

DETAILED DESCRIPTION OF THE PREFERRED EMBODIMENT

Figure 1:
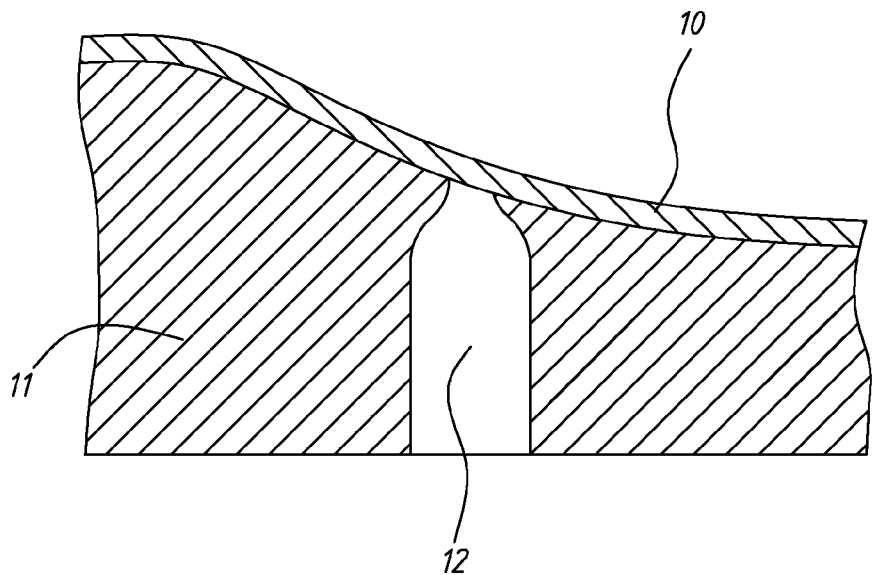
FIG. 1 is a schematic sectional view showing a sinus floor performed with a surgical operation of osteotomy, and an opening formed by drilling on a cortical bone.
Figure 2:
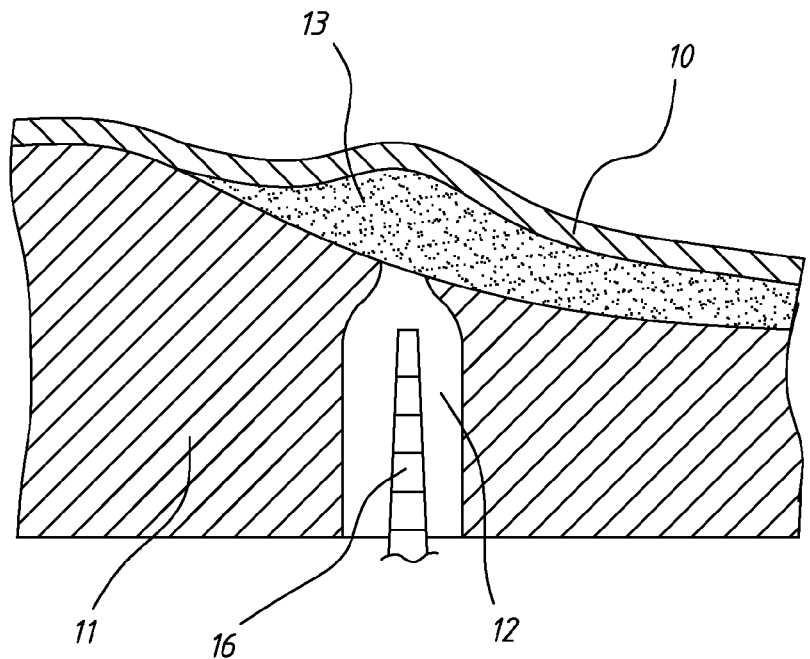
FIG. 2 is a schematic sectional view showing a conventional bone powder filling tool used to fill bone powder into an area below a separated and lifted nasal sinus floor.
Figure 3:
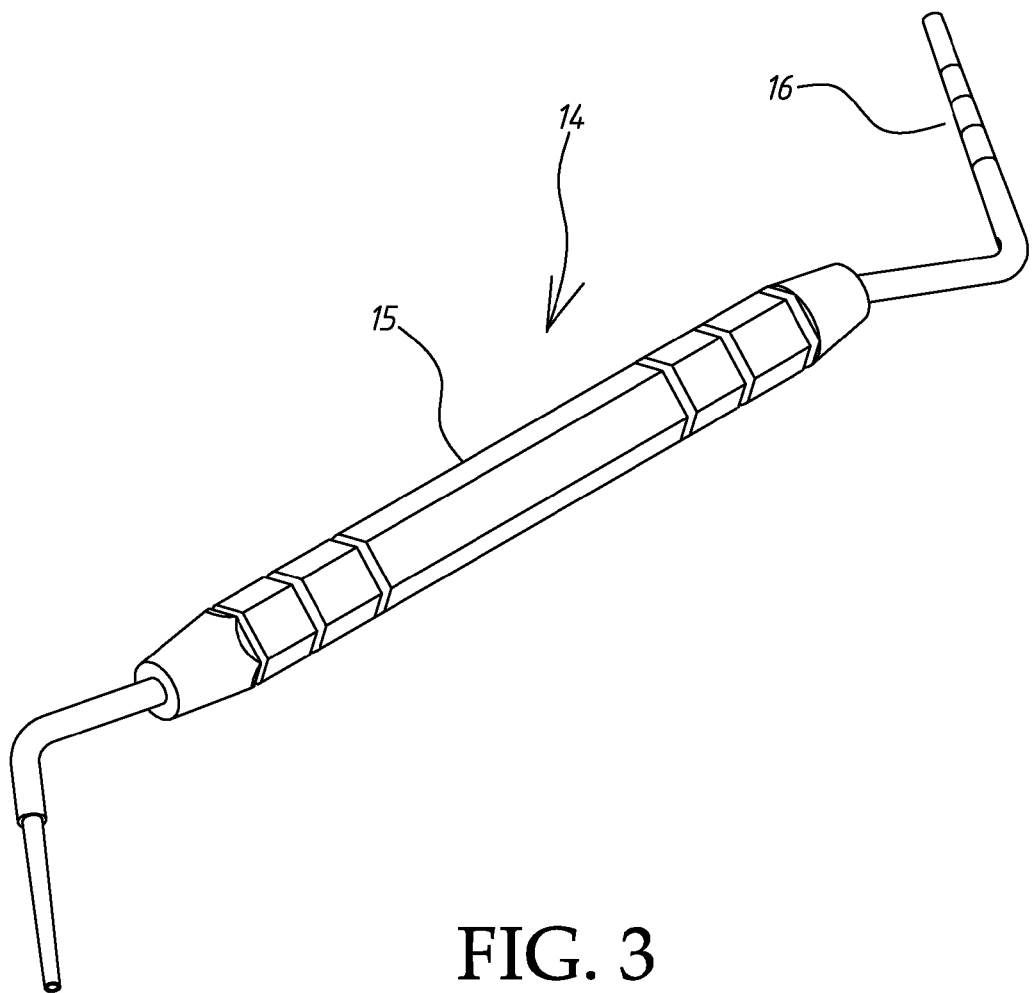
FIG. 3 is a perspective view of a conventional bone powder filling tool.
Figure 4:
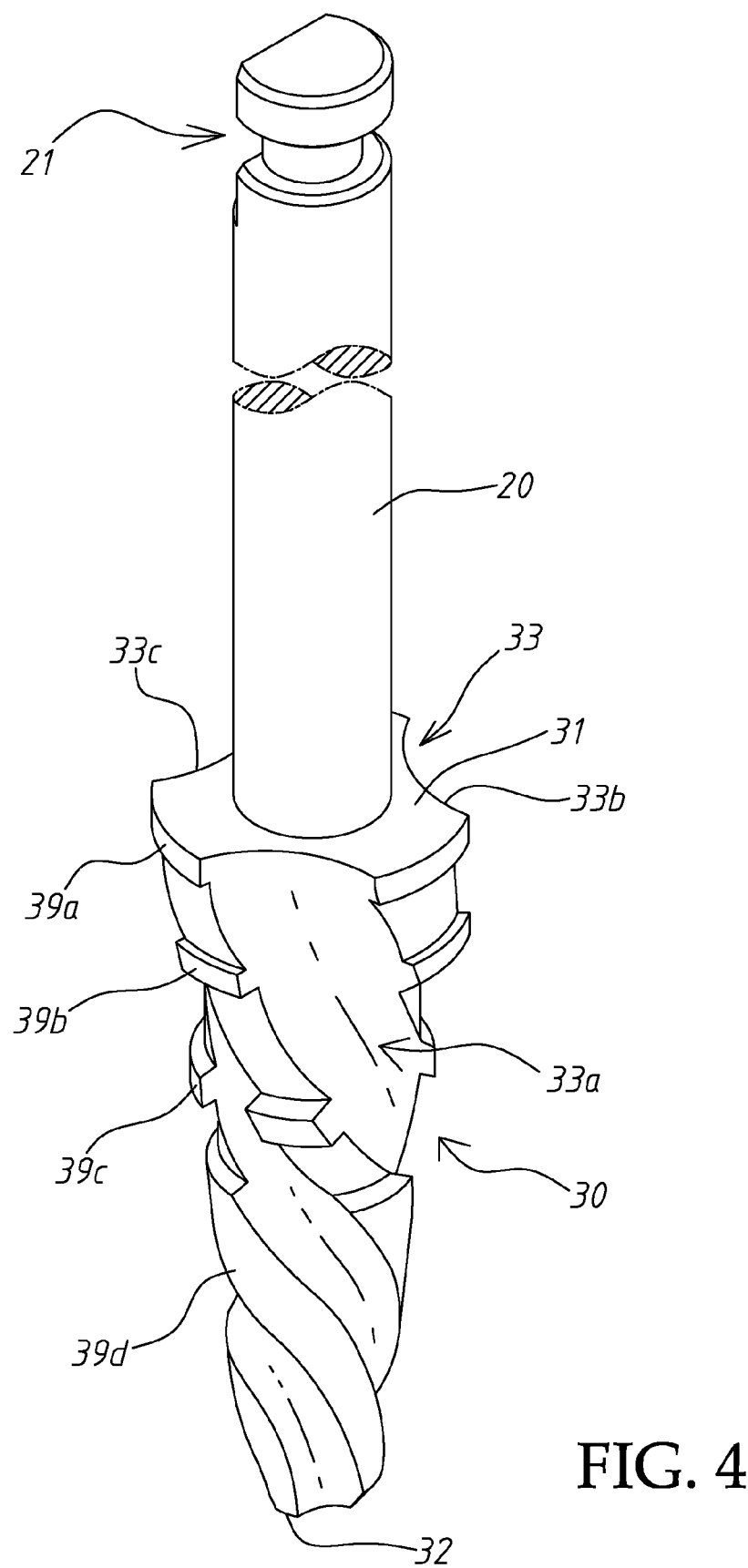
FIG. 4 is a perspective view of a bone powder filling tool in accordance with the present invention.
Figure 5:
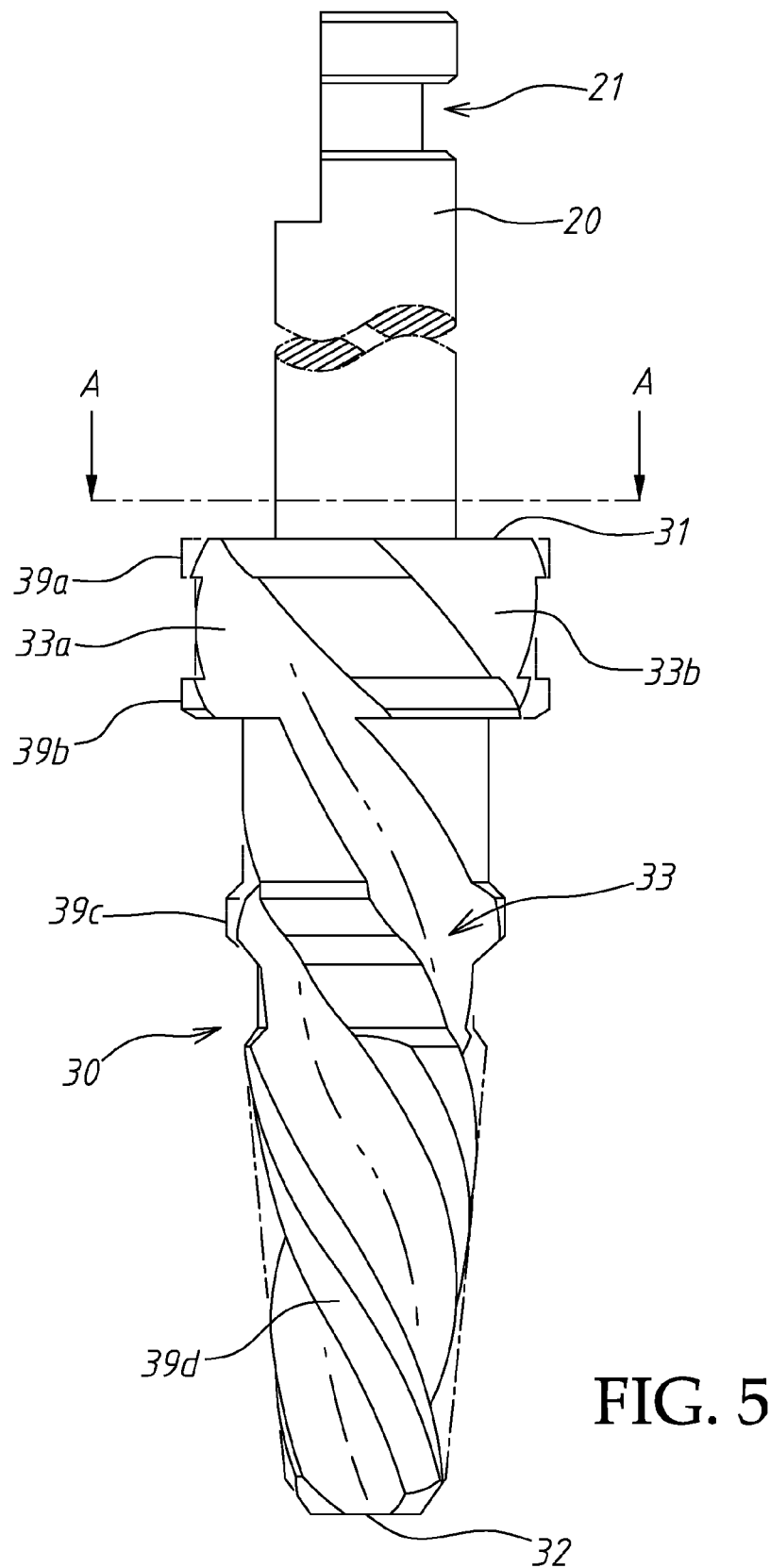
FIG. 5 is a front view of the bone powder filling tool in accordance with the present invention.
Figure 6:
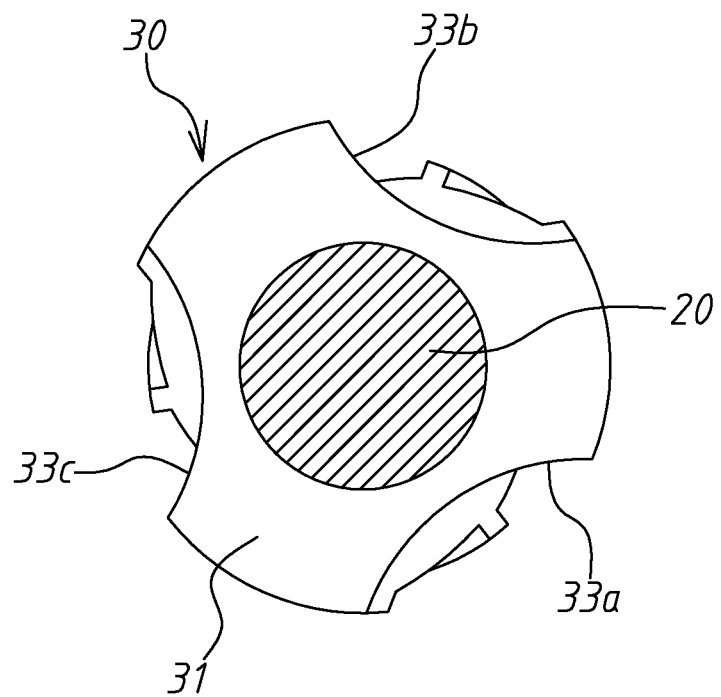
FIG. 6 is an end view of the bone powder filling tool in accordance with the present invention.

Referring to FIGS. 4-6, a bone powder filling tool in accordance with the present invention is shown. The bone powder filling tool comprises a handle 20, and a bone powder propelling bit 30 axially and integrally located one end of the handle 20. The handle 20 has its one end connected with the bone powder propelling bit 30, and its other end provided with a connection member 21 connectable to a pneumatic or electric rotary dental instrument to be operated to rotate the bone powder filling tool.

According to the present preferred embodiment, the bone powder propelling bit 30 comprises opposing top end portion 31 and bottom end portion 32, and at least one bone powder transferring groove 33 located on the periphery thereof and extending from the top end portion 31 to the bottom end portion 32. Preferably, the bone powder transferring groove 33 extends spirally around the periphery of the bone powder propelling bit 30. Further, the top end portion 31 of the bone powder propelling bit 30 is 5 fixedly connected to one end of the handle 20 opposite to the connection member 21 and has a diameter greater than the handle 20.

According to the present preferred embodiment, the bone powder propelling bit 30 comprises three bone powder transferring grooves 33a, 33b and 33c respectively spirally extend around the periphery thereof and kept apart from one another.

Further, the bone powder propelling bit 30 has a transverse (radial) width gradually reducing from the top end portion 31 toward the bottom end portion 32.

According to the preferred embodiment of the present invention, as illustrated in the annexed drawings, the bone powder propelling bit 30 further comprises a plurality of bone powder propelling threads 39a, 39b, 39c and 39d extending around the periphery at different elevations. Unlike the threads of a regular drill bit for propelling cutting chips in a direction reversed to the drilling direction, the bone powder propelling threads 39a, 39b, 39c and 39d are adapted for propelling applied bone powder forwardly into the expected bone powder filling area under the nasal sinus floor when the bone powder filling tool is being driven forwardly into the cortical bone under the nasal sinus floor. Further, the bone powder propelling threads 39a, 39b, 39c, 39d are so designed that the depth (transverse width) of one upper bone powder propelling thread is relatively greater than an adjacent lower bone powder propelling thread.

Figure 7:
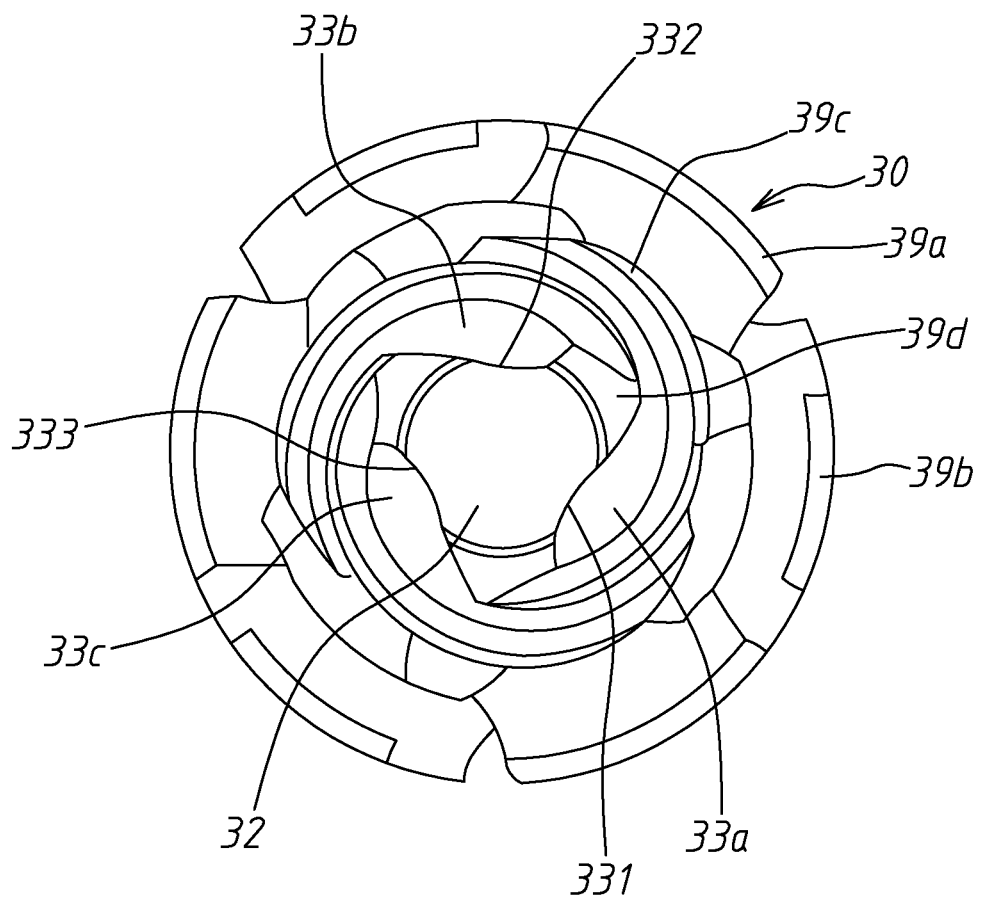
FIG. 7 is a sectional view taken along line A-A of FIG. 5.

Referring to FIG. 7, the bone powder transferring grooves 33a, 33b and 33c are equally spaced from one another around the periphery of the bone powder propelling bit 30, each defining a respective outlet 331, 332 and 333. The outlets 331, 332 and 333 of the bone powder transferring grooves 33a, 33b and 33c are equiangularly distributed in the bottom end portion 32 of the bone powder propelling bit 30.

Further, the bottom end portion 32 of the bone powder propelling bit 30 is preferably sleek, blunt-nosed, avoiding damage to the cortical bone or nasal sinus floor during application. Further, the bone powder propelling threads 39a, 39b, 39c and 39d can be chamfered.

Figure 8:
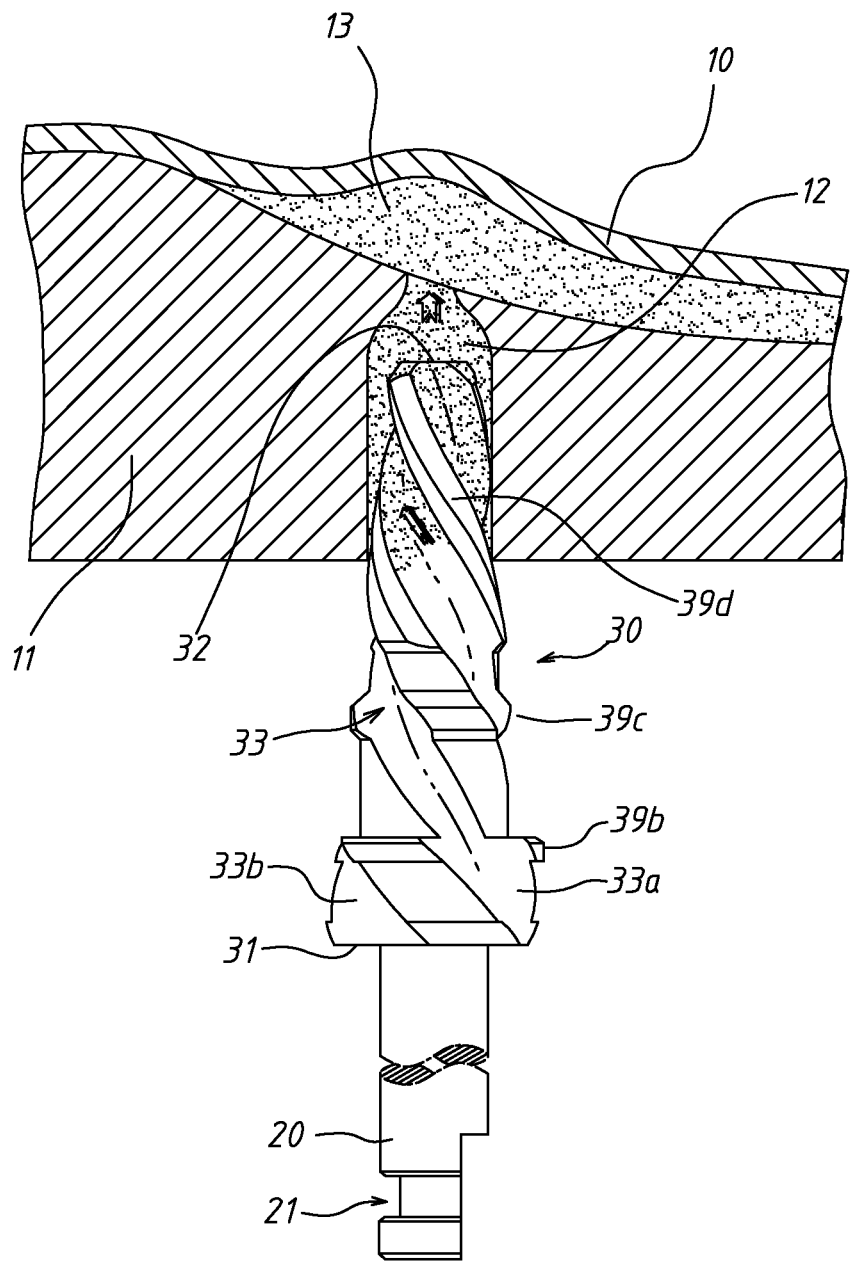
FIG. 8 is a schematic sectional view showing a the bone powder filling tool used to fill bone powder into an area below a separated and lifted nasal sinus floor in accordance with the present invention.

During application of the bone powder filling tool in a dental surgery, as shown in FIG. 8, a block form bone powder 13 is placed on the front side of the bone powder filling tool, and then the bone powder filling tool is rotated to force the block form bone powder 13 into an opening 12 in the cortical bone 11 below the nasal sinus floor 10. Subject to the design of the bone powder transferring grooves 33a, 33b and 33c to match with the design of the bone powder propelling threads 39a, 39b, 39c and 39d, the bone powder 13 can be rapidly and uniformly propelled into the space between the sinus floor 10 and the cortical bone 11 to increase the thickness of the cortical bone 11 in favor of the process of the subsequent tooth implanting. Further, as shown in FIG. 8, the bone powder transferring grooves 33a, 33b and 33c have a transverse (radial) width gradually increasing in direction from the bottom end portion 32 of the bone powder filling tool toward the top end portion 31 thereof.

Figure 9:
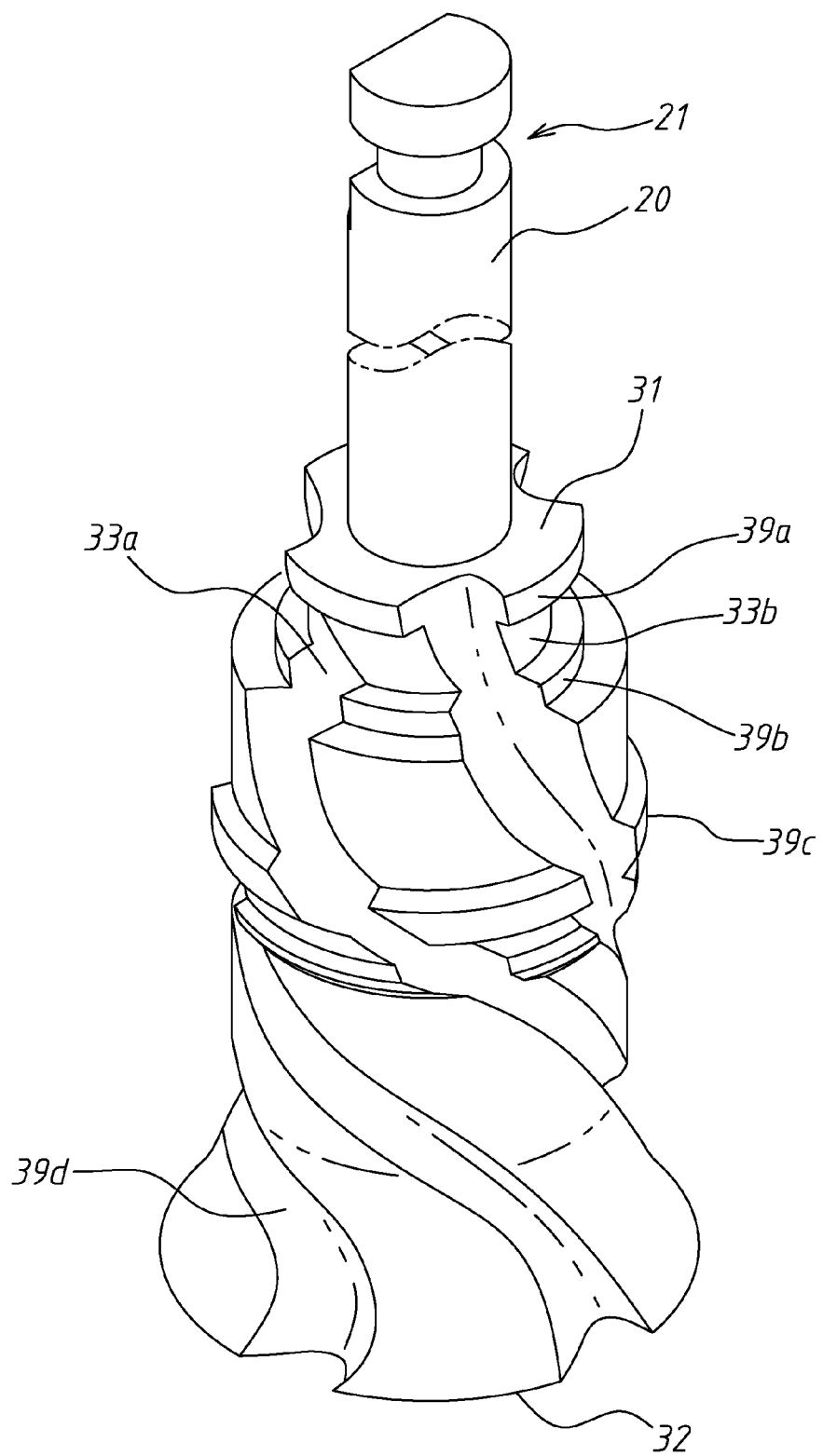
FIG. 9 is a perspective view of a bone powder filling tool in accordance with the present invention.
Figure 10:
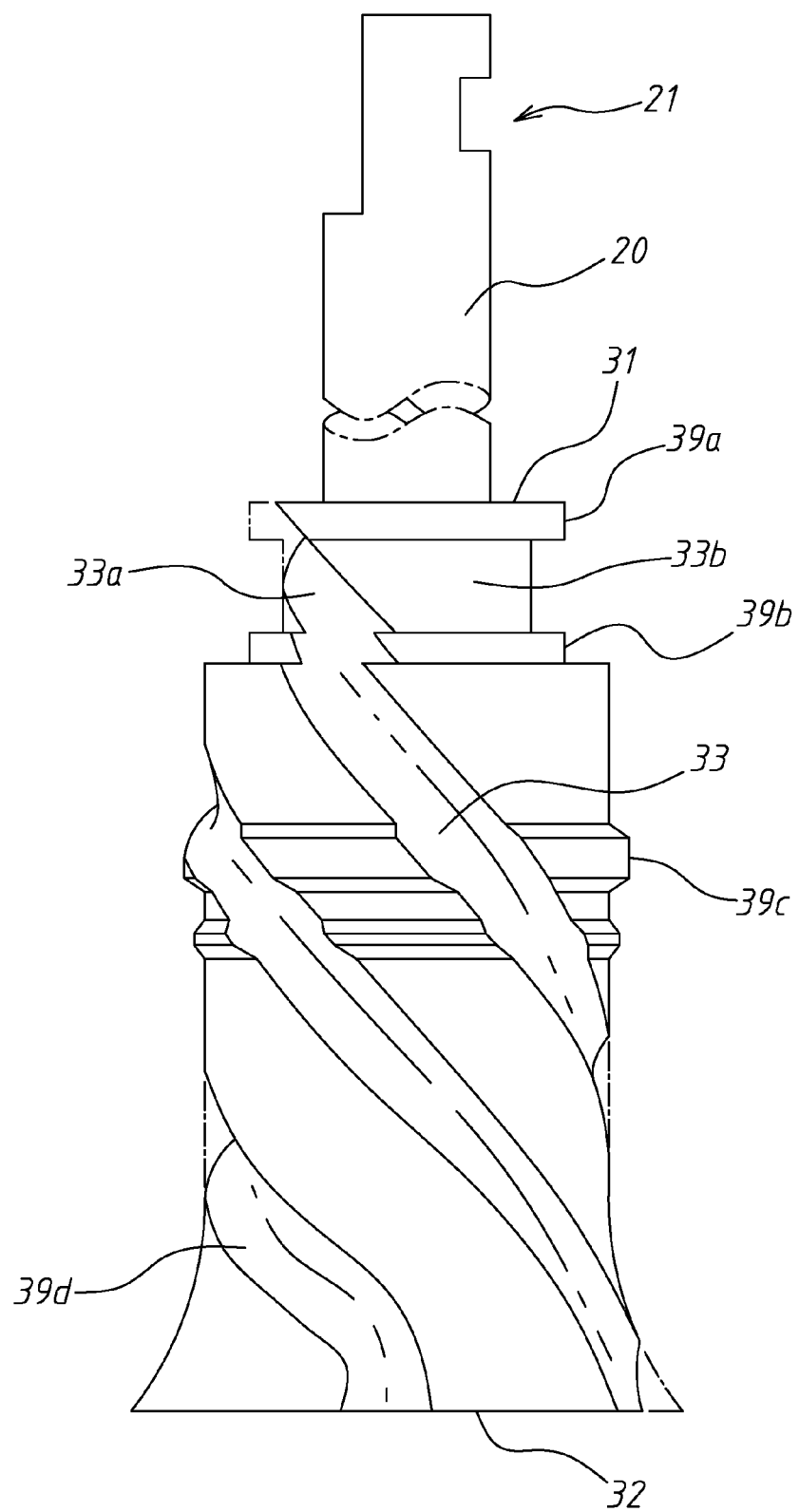
FIG. 10 is a front view of the bone powder filling tool in accordance with the present invention.

FIGS. 9 and 10 depict another embodiment of the bon powder propelling bit of the invention. Referring to FIGS. 9 and 10, the bone powder propelling bit 30 has a transverse (radial) width gradually increasing from the top end portion 31 toward the bottom end portion 32 which is a flat wall. The bone powder propelling bit 30 further comprises a plurality of bone powder propelling threads 39a, 39b, 39c and 39d extending around the periphery at different elevations. Unlike the threads of a regular drill bit for propelling cutting chips in a direction reversed to the drilling direction, the bone powder propelling threads 39a, 39b, 39c and 39d are adapted for propelling applied bone powder forwardly into the expected bone powder filling area under the nasal sinus floor when the bone powder filling tool is being driven forwardly into the cortical bone under the nasal sinus floor. The bone powder transferring grooves 33a, 33b and 33c are equally spaced from one another around the periphery of the bone powder propelling bit 30, each defining a respective outlet 331, 332 and 333. The outlets 331, 332 and 333 of the bone powder transferring grooves 33a, 33b and 33c are equiangularly distributed in the bottom end portion 32 of the bone powder propelling bit 30.

As stated above, the design of the bone powder transferring grooves and bone powder propelling threads of the bone powder filling tool can rapidly and uniformly propel the applied bone powder into the space between the sinus floor and the cortical bone to increase the thickness of the cortical bone in favor of the process of the subsequent tooth implanting, helping the doctor in charge of the operation save operating time and physical strength.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A bone powder filling tool configured for use with a rotary dental instrument, said bone powder filling tool comprising: a handle, and a bone powder propelling bit axially and integrally located one end of said handle, said handle having one end thereof connected with said bone powder propelling bit and an opposite end thereof provided with a connection member connectable to said rotary dental instrument to be operated to rotate said bone powder filling tool, said bone powder propelling bit comprising opposing top end portion and bottom end portion, at least one bone powder transferring groove located on a periphery thereof and extending from said top end portion to said bottom end portion, and a plurality of bone powder propelling threads being spaced apart along a length of said bone powder propelling bit between said top end portion and said bottom end portion thereof, each of said plurality of bone powder propelling threads are a radial ring extending around the periphery of said bone powder propelling bit and located at a different elevation relative to elevations of adjacent ones of said plurality of bone powder propelling threads, wherein the bond power filling tool configured for propelling an applied bone powder in a direction from said top end portion toward said bottom end portion.

2. The bone powder filling tool as claimed in claim 1, wherein each said bone powder transferring groove extends spirally around the periphery of said bone powder propelling bit from said top end portion to said bottom end portion.

3. The bone powder filling tool as claimed in claim 2, wherein said bone powder propelling bit comprises a plurality of bone powder transferring grooves spirally extending around the periphery thereof and kept apart from one another.

4. The bone powder filling tool as claimed in claim 1, wherein said bone powder propelling bit has a transverse (radial) width gradually reducing from said top end portion toward said bottom end portion.

5. The bone powder filling tool as claimed in claim 1, wherein said bottom end portion of said bone powder propelling bit is blunt-nosed.

6. The bone powder filling tool as claimed in claim 1, wherein said bone powder propelling bit has a transverse (radial) width gradually increasing from said top end portion toward said bottom end portion.

7. The bone powder filling tool as claimed in claim 1, wherein said bottom end portion of said bone powder propelling bit is a flat wall.

* * * * *